United States Patent
Ishikawa

(10) Patent No.: US 9,144,519 B2
(45) Date of Patent: Sep. 29, 2015

(54) METHOD FOR PRODUCING TAMPON AND APPARATUS FOR PRODUCING TAMPON

(75) Inventor: Yoshihide Ishikawa, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 514 days.

(21) Appl. No.: 13/579,621

(22) PCT Filed: Feb. 17, 2011

(86) PCT No.: PCT/JP2011/053355
§ 371 (c)(1),
(2), (4) Date: Oct. 22, 2012

(87) PCT Pub. No.: WO2011/105276
PCT Pub. Date: Sep. 1, 2011

(65) Prior Publication Data
US 2013/0036584 A1 Feb. 14, 2013

(30) Foreign Application Priority Data

Feb. 23, 2010 (JP) ................. 2010-037848

(51) Int. Cl.
*A61F 13/20* (2006.01)
(52) U.S. Cl.
CPC ................. *A61F 13/2085* (2013.01)
(58) Field of Classification Search
CPC . A61F 13/2088; A61F 13/34; A61F 13/2085; A61F 13/2082; A61F 13/2097
USPC ............ 28/120, 118, 119; 289/1.5, 13–15, 17
See application file for complete search history.

(56) References Cited

U.S. PATENT DOCUMENTS

| | | | | |
|---|---|---|---|---|
| 2,361,783 A | * | 10/1944 | McLaughlin | 53/397 |
| 2,462,178 A | * | 2/1949 | Ganz | 28/120 |
| 2,532,438 A | * | 12/1950 | Behr | 156/88 |
| 2,624,078 A | | 1/1953 | Winter et al. | |
| 2,690,598 A | * | 10/1954 | Bletzinger et al. | 53/399 |
| 3,477,102 A | * | 11/1969 | Etz | 28/120 |
| 4,019,226 A | * | 4/1977 | Yamauchi et al. | 28/120 |
| 4,836,587 A | | 6/1989 | Hinzmann | |

(Continued)

FOREIGN PATENT DOCUMENTS

| | | |
|---|---|---|
| DE | 2355962 B1 | 2/1975 |
| JP | 53148895 A | 12/1978 |

(Continued)

OTHER PUBLICATIONS

Office Action mailed Aug. 27, 2013, corresponds to Japanese patent application No. 2010-037848.

(Continued)

*Primary Examiner* — Amy Vanatta
(74) *Attorney, Agent, or Firm* — Lowe Hauptman & Ham, LLP

(57) ABSTRACT

The present invention provides a method for producing a tampon having an absorbent body that absorbs fluid and a string that is attached to the absorbent body, the method includes: attaching the string to the absorbent body; causing a regulation section to regulate movement of the absorbent body; causing a holding section to hold the string; and applying a tensile force to the string by increasing a distance in a longitudinal direction of the absorbent body between the regulation section and the holding section.

8 Claims, 11 Drawing Sheets

(56) References Cited

U.S. PATENT DOCUMENTS

| | | | |
|---|---|---|---|
| 5,084,038 A * | 1/1992 | Sheldon et al. | 604/358 |
| 5,566,435 A * | 10/1996 | Brown, Jr. | 28/120 |
| 7,011,033 B2 | 3/2006 | Sargent, Jr. et al. | |
| 2003/0131455 A1 * | 7/2003 | Rajala et al. | 28/120 |
| 2007/0175372 A1 | 8/2007 | Kondo et al. | |
| 2007/0193486 A1 * | 8/2007 | Kondo et al. | 112/2 |
| 2008/0035040 A1 * | 2/2008 | Aoyama et al. | 112/475.08 |
| 2011/0273727 A1 * | 11/2011 | Seki et al. | 356/634 |

FOREIGN PATENT DOCUMENTS

| | | |
|---|---|---|
| JP | 57173054 A | 10/1982 |
| JP | 60116350 A | 6/1985 |
| JP | 62286460 A | 12/1987 |
| JP | 63154175 A | 6/1988 |
| JP | 2000042031 A | 2/2000 |
| JP | 2006527640 A | 12/2006 |
| WO | 2005004774 A1 | 1/2005 |

OTHER PUBLICATIONS

International Search Report for PCT/JP2011/053355, dated May 17, 2011.

Extended European Search Report issued Feb. 26, 2014 corresponds to European Patent application No. 11747240.7.

* cited by examiner

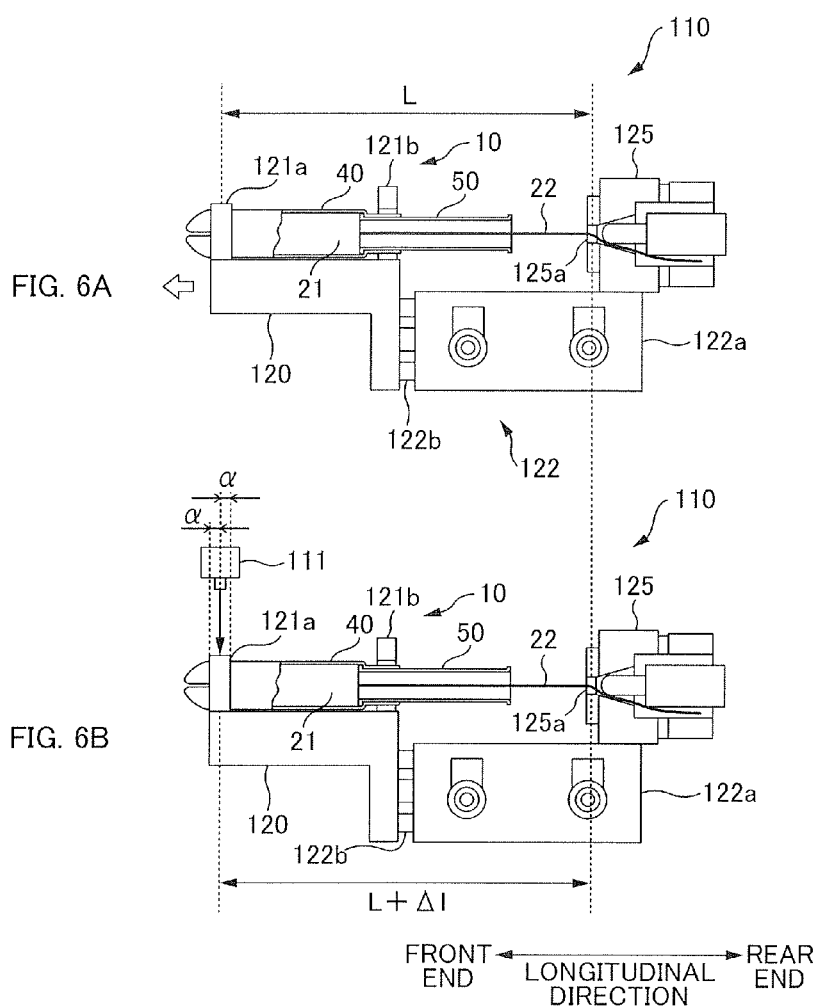
FIG. 6A
FIG. 6B
FRONT END ← LONGITUDINAL DIRECTION → REAR END
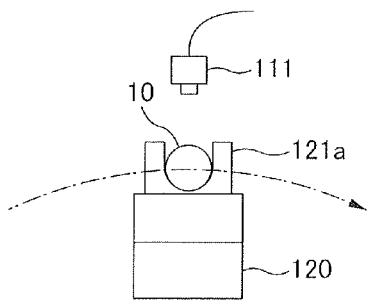
FIG. 6C

FRONT END ←— LONGITUDINAL DIRECTION —→ REAR END

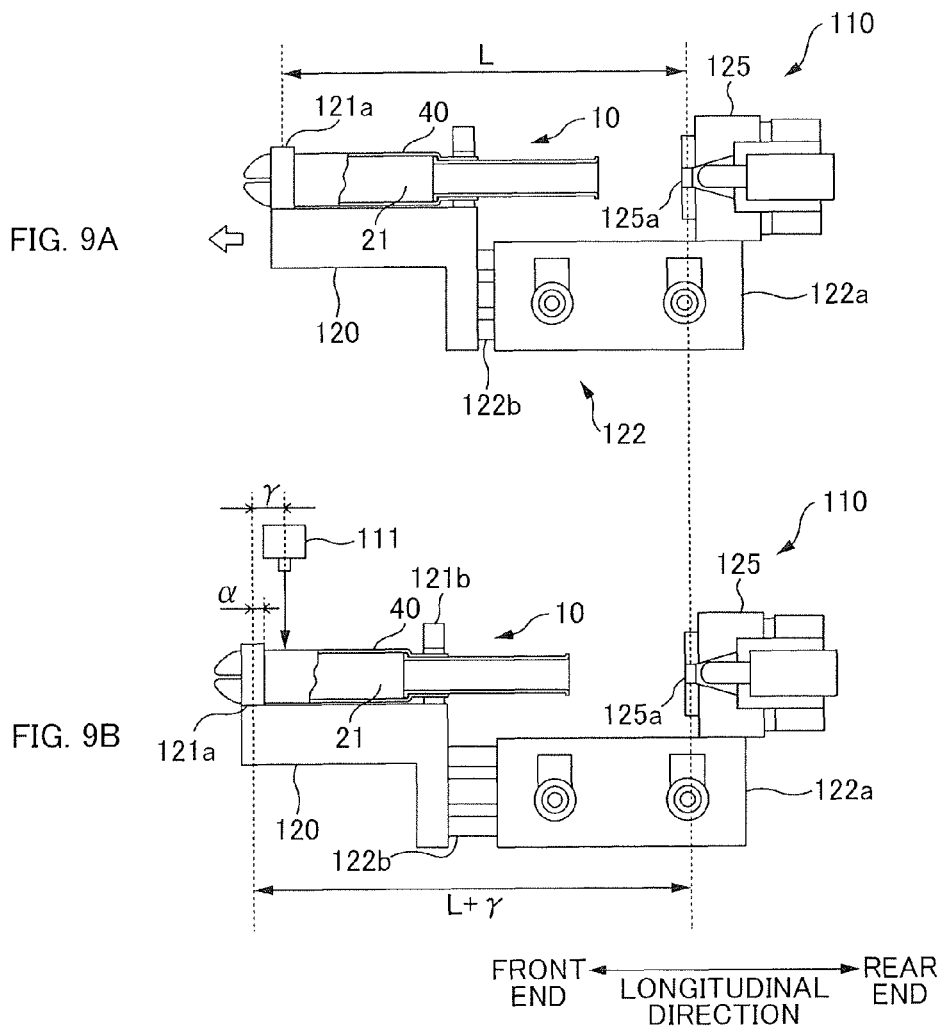
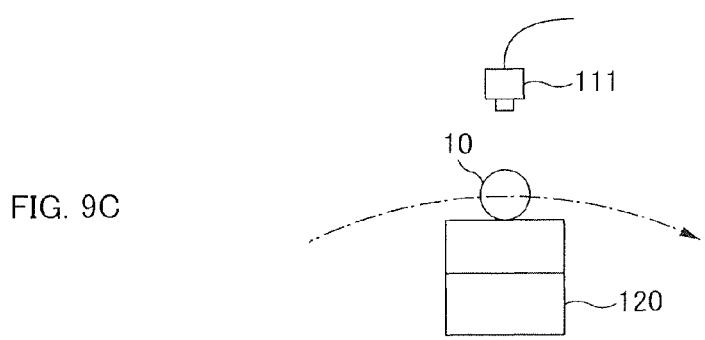
FIG. 9A
FIG. 9B
FIG. 9C

FRONT END ←— LONGITUDINAL DIRECTION —→ REAR END

METHOD FOR PRODUCING TAMPON AND APPARATUS FOR PRODUCING TAMPON

RELATED APPLICATIONS

The present application is National Phase of International Application Number PCT/JP2011/053355, filed Feb. 17, 2011, and claims priority from Japanese Application Number 2010-037848, filed Feb. 23, 2010.

TECHNICAL FIELD

The present invention relates to methods for producing a tampon and apparatuses for producing a tampon.

BACKGROUND ART

Tampons are widely known as sanitary goods. In a tampon, a string is attached to one end of an absorbent body that absorbs fluid such as menstrual blood. This string is pulled by a user when removing the absorbent body that has been inserted into the vaginal cavity out of the vaginal cavity.

A tampon producing method has been proposed in which, when attaching a string to an absorbent body, a string supply portion checks whether or not a string has a defect such as knots or pills, and eliminates a tampon with a defective string attached from the production line (see Patent Document 1, for example).

CITATION LIST

Patent Literature

PTL 1: JP-A-2000-42031

SUMMARY OF INVENTION

Technical Problem

However, with the above-described method, since a defect of a string itself is checked, an abnormality which arises after the string has been attached to an absorbent body cannot be checked. For example, abnormalities such as the string not being reliably sewn on the absorbent body or the string being damaged in the production line cannot be checked. That is to say, there is a problem in that the string may not be properly attached to the absorbent body.

The invention was made in view of such a problem, and it is an advantage thereof to provide a tampon producing method and a tampon producing apparatus that enable a string to be properly attached to an absorbent body.

Solution to Problem

In order to achieve the above-described advantage, a primary aspect of the invention is directed to a method for producing a tampon including an absorbent body that absorbs fluid, and a string that is attached to the absorbent body, the method including the steps of: attaching the string to the absorbent body; causing a regulation section to regulate movement of the absorbent body; causing a holding section to hold the string; and applying a tensile force to the string by increasing a distance in a longitudinal direction of the absorbent body between the regulation section and the holding section.

Features of the invention other than the above will become clear by reading the description of the present specification with reference to the accompanying drawings.

Advantageous Effects of Invention

The invention provides a tampon producing method and a tampon producing apparatus that enable a string to be properly attached to an absorbent body.

BRIEF DESCRIPTION OF DRAWINGS

FIGS. 6A to 6C show views illustrating a test result in a case where a string has been properly attached to an absorbent body.

FIGS. 9A to 9C show views illustrating a test result in a case where a string has not been attached to an absorbent body.

DESCRIPTION OF EMBODIMENTS

Figure 1A:
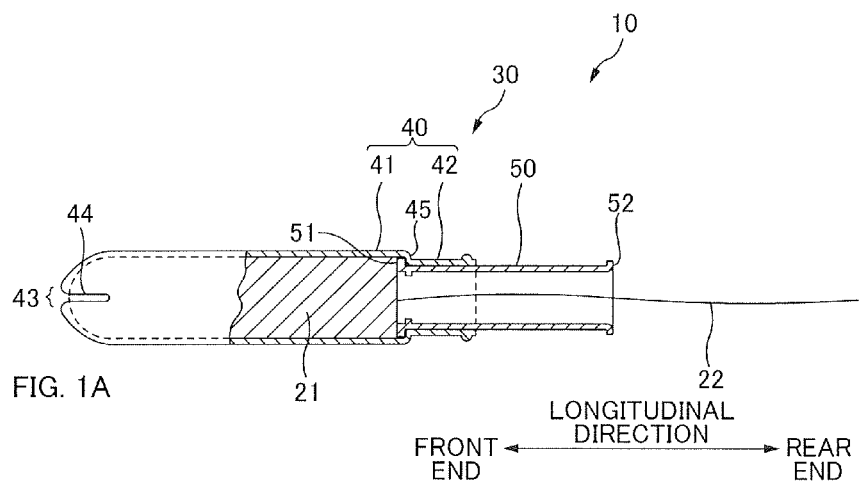
FIG. 1A shows a cross-sectional view of constituent elements of a tampon.

At least the following matters will be made clear by the explanation in the present specification and the description of the accompanying drawings.

A method for producing a tampon including an absorbent body that absorbs fluid, and a string that is attached to the absorbent body, the method includes: attaching the string to the absorbent body; causing a regulation section to regulate movement of the absorbent body; causing a holding section to hold the string; and applying a tensile force to the string by increasing a distance in a longitudinal direction of the absorbent body between the regulation section and the holding section.

According to this method for producing a tampon, it can be checked whether or not the string has been properly attached to the absorbent body.

In this method for producing a tampon, the tampon has an applicator provided with an outer tube that contains the absorbent body and an inner tube that moves inside the outer tube and pushes out the absorbent body from a front end of the outer tube, the string is exposed from a rear end of the inner tube, and the regulation section regulates movement of the applicator and regulates movement of the absorbent body via an end face of the inner tube.

According to this method for producing a tampon, it can be checked whether or not the string has been properly attached to the absorbent body.

In this method for producing a tampon, an attachment failure of the string with respect to the absorbent body is checked based on an amount of change in the distance in the longitudinal direction between the regulation section and the holding section before and after increasing the distance.

According to this method for producing a tampon, it can be determined whether or not the string has been properly attached to the absorbent body.

In this method for producing a tampon, a defective product discharge section is provided that discharges out of a production process the tampon in which there is an attachment failure of the string with respect to the absorbent body, as a result of increasing the distance, and the method further includes: calculating a point in time when a given tampon reaches the defective product discharge section; and causing the defective product discharge section to discharge out of the production process the given tampon at the calculated point in time, in a case where there is an attachment failure of the string with respect to the absorbent body of the given tampon.

According to this method for producing a tampon, a product with an attachment failure of the string with respect to the absorbent body can be discharged out of the production process, and a product in which the string has been properly attached to the absorbent body can be provided.

In this method for producing a tampon, one of the regulation section and the holding section is taken as a fixed section whose position is fixed, another one of the regulation section and the holding section is taken as a movable section that can move in the longitudinal direction, a sensor is positioned at a location that is off the fixed section toward the movable section by a predetermined distance, and an attachment failure of the string with respect to the absorbent body is checked based on a detection result of the sensor after the distance is increased.

According to this method for producing a tampon, it can be determined whether or not the string has been properly attached to the absorbent body.

In this method for producing a tampon, the movable section is positioned at a location where the sensor detects the movable section before the distance is increased, and the movable section is positioned at a location where the sensor does not detect the movable section after the distance is increased, in a case where there is an attachment failure of the string.

According to this method for producing a tampon, a product in which there is an attachment failure of the string with respect to the absorbent body can be detected.

In this method for producing a tampon, the movable section is positioned at a location where the sensor detects the movable section before the distance is increased, and the movable section is positioned at a location where the sensor detects the movable section after the distance is increased, in a case where the string has been properly attached and is held with slack by the holding section.

According to this method for producing a tampon, even when the string is held with slack, in the case that the string has been properly attached, that product is determined as a product in which the string has been properly attached.

In this method for producing a tampon, the string is held by the holding section while air is sucked by a suction section from a side of the absorbent body from which the string is extended.

According to this method for producing a tampon, the holding section can hold the string while suppressing slack in the string.

Furthermore, the invention is directed to an apparatus for producing a tampon including an absorbent body that absorbs fluid, and a string that is attached to the absorbent body, the apparatus includes: an attachment device that attaches the string to the absorbent body; a regulation section that regulates movement of the absorbent body; a holding section that holds the string; and a test device that applies a tensile force to the string by increasing a distance in a longitudinal direction of the absorbent body between the regulation section and the holding section.

According to this tampon producing apparatus, a product in which the string has been properly attached to the absorbent body can be provided.

Regarding the Configuration of a Tampon

First, the configuration of a tampon 10 will be described.

Figure 1B:
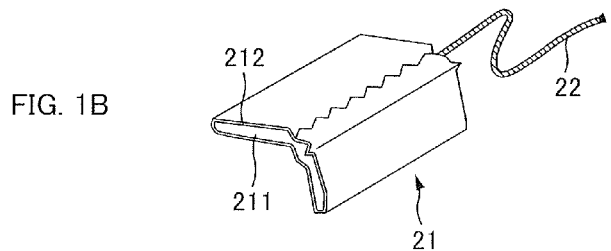
FIG. 1B shows a view of the manner in which a string is attached to an absorbent body to become a tampon main body.
Figure 1C:
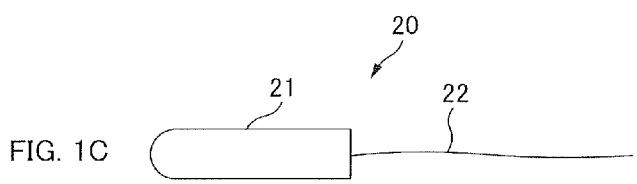
FIG. 1C shows an external view of the tampon main body.

FIG. 1A shows a cross-sectional view of constituent elements of the tampon 10, FIG. 1B shows a view of the manner in which a string 22 is attached to an absorbent body 21 to form into a tampon main body 20, and FIG. 1C shows an external view of the tampon main body 20. Note that, in the following description, the side in the longitudinal direction of the tampon 10 that is to be inserted into the vaginal cavity is referred to as a front end, and the opposite side is referred to as a rear end.

As shown in FIG. 1, the tampon 10 of this embodiment has the tampon main body 20 and an applicator 30. The applicator 30 is provided with an outer tube member 40 (corresponding to an outer tube) that contains the tampon main body 20 and a movable member 50 (corresponding to an inner tube) that is used to move the tampon main body 20 relative to the outer tube member 40. The applicator 30 is an auxiliary unit for making it easy to guide the tampon main body 20 into the vaginal cavity.

The tampon main body 20 is for blocking the vaginal cavity and absorbing fluid such as menstrual blood, and has the absorbent body 21 and the string 22. For example, the absorbent body 21 has a configuration in which an absorbent body material 211 (cotton portion) having absorbent fiber layers mainly made of rayon is covered by a cover member 212 made of polyester spunbonded nonwoven fabric, and is shaped into a bullet.

As shown in FIG. 1B, the string 22 is sewn on the absorbent body 21. The string 22 is, for example, a twisted string made of cotton. The string 22 is extended from the rear end side of the absorbent body 21, and is held by, for example, the user of the tampon 10 when pulling the absorbent body 21 inside the vaginal cavity out of the vaginal cavity. Furthermore, as shown in FIG. 1A, the string 22 is extended inside the applicator 30, that is, inside the outer tube member 40 and the tube-shaped movable member 50 which are tube-shaped, and is exposed at the rear end of the applicator 30.

The outer tube member 40 is for containing the tampon main body 20 in a relatively movable manner. The outer tube member 40 is a tubular body formed by injection molding using a thermoplastic resin (e.g., polyethylene resin), and has an appropriate flexibility. Furthermore, the outer tube member 40 is provided with a large-diameter section 41 at the front end side and a small-diameter section 42 at the rear end side. The inner diameter (and the outer diameter) of the large-diameter section 41 are larger than the inner diameter (and the outer diameter) of the small-diameter section 42. Accordingly, a ring-like stepped portion 45 is formed between the large-diameter section 41 and the small-diameter section 42.

The large-diameter section 41 has a function of containing the tampon main body 20, and when using the tampon 10, is inserted into the vaginal cavity in a state where the large-diameter section 41 contains the tampon main body 20. Furthermore, a plurality of incisions 44 are made in the front end section of the large-diameter section 41, forming into an openable portion (hereinafter, referred to as a "front end opening 43"). Thus, when the outer tube member 40 is inserted into the vaginal cavity and then the tampon main body 20 is pressed by the movable member 50 (described later), the front end opening 43 is spread out through the application of pressure from the tampon main body 20, and the tampon main body 20 is exposed through the outer tube member 40. After the tampon main body 20 is pushed out of the outer tube member 40, the user of the tampon 10 removes the applicator 30 out of the vaginal cavity, which completes wearing of the tampon main body 20.

The small-diameter section 42 functions as a guide portion that guides the movable member 50 when the movable member 50 is moving inside the small-diameter section 42. Furthermore, the small-diameter section 42 is a portion that is held by the user when wearing the tampon 10.

The movable member 50 can move in the longitudinal direction inside the outer tube member 40, and is used to push the tampon main body 20 out of the outer tube member 40 from the front end opening 43. Note that the front end of the movable member 50 is formed as a catch section 51 having an outer diameter larger than the inner diameter of the small-diameter section 42. That is, the catch section 51 is configured such that, when the movable member 50 is pulled to the rear end side, the catch section 51 is brought into contact with the stepped portion 45 of the outer tube member 40, and therefore the movable member 50 is not detached from the outer tube member 40. Meanwhile, a ring-like protrusion 52 is disposed at the rear end of the movable member 50. The ring-like protrusion 52 is configured such that, when the movable member 50 is pressed to the front end side, the ring-like protrusion 52 is brought into contact with the rear end of the small-diameter section 42 of the outer tube member 40, and therefore the movable member 50 is not detached from the outer tube member 40.

Regarding Method for Producing the Tampon 10

Figure 2:
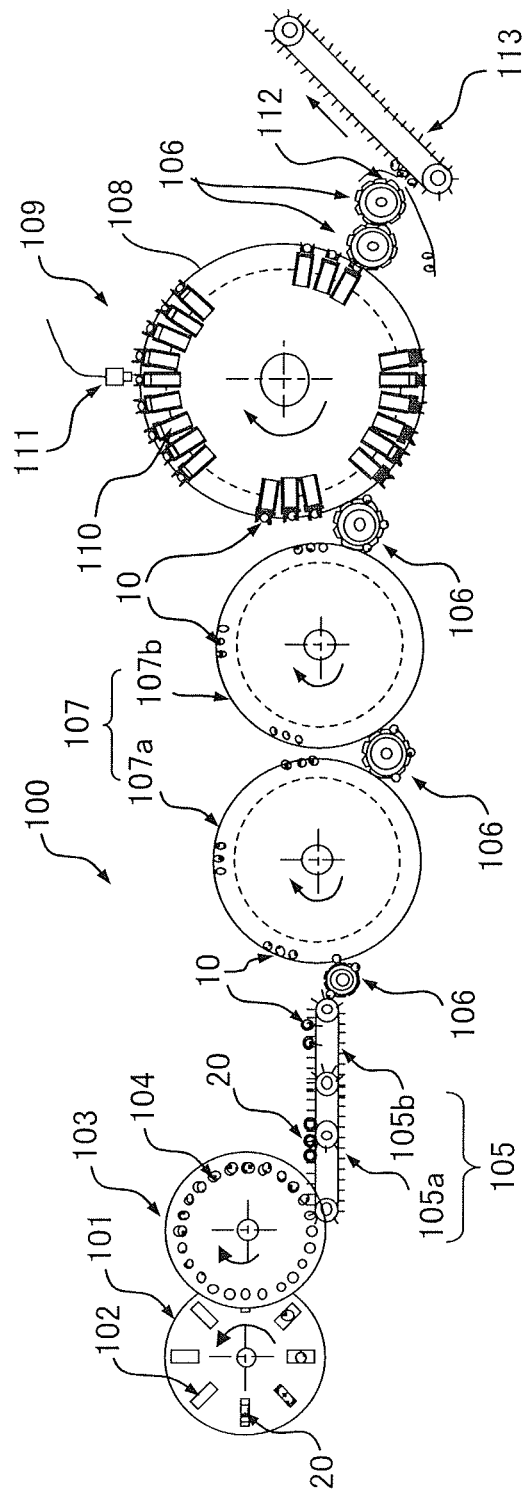
FIG. 2 shows a schematic view of a tampon producing apparatus viewed from the front.
Figure 3:
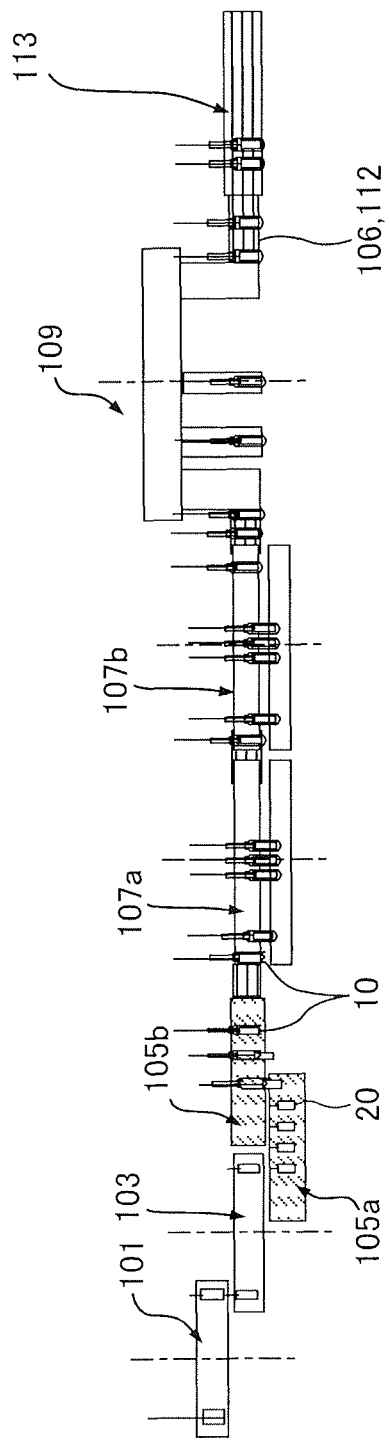
FIG. 3 shows a schematic view of the tampon producing apparatus viewed from above.

Next, a production method for producing the above-described tampon 10 will be described. FIG. 2 is a schematic view of a tampon producing apparatus 100 viewed from the front. FIG. 3 shows a schematic view of the tampon producing apparatus 100 viewed from above. FIG. 4 shows schematic views of a defective product discharge section 112. Note that the tampon main body 20 and the applicator 30 are produced in separate processes and then assembled into the tampon 10.

As shown in FIG. 2, the tampon producing apparatus 100 has a compression molding drum 101 that forms the absorbent body 21 of the tampon main body 20, a heat drum 103 that heats the absorbent body 21, an assembly unit 105 that assembles the tampon main body 20 and the applicator 30, a heating drum 107a that heats the front end opening 43 of the outer tube member 40 containing the tampon main body 20 while curving the front end opening 43 in the closing direction, a cooling drum 107b that cools down the front end opening 43 while maintaining the curved shape, a "string test unit 109" that tests whether or not the string 22 has been properly attached to the absorbent body 21 while transporting the tampon 10 on a rotating drum 108, and the defective product discharge section 112. In this description, devices for molding the applicator 30 and the like are omitted.

First, as shown in FIG. 1B, the absorbent body material 211 for forming into a base material of the absorbent body 21 is covered by the cover member 212 and cut into a predetermined shape and size. The string 22 is attached to (sewn on) the cover member 212 and the absorbent body material 211 (the absorbent body 21) that have been cut using an attachment device (not shown). The string 22 is sewn on the absorbent body 21 from the front end to the rear end in the longitudinal direction. Subsequently, the tampon main body 20 is inserted into a retaining mechanism 102, a plurality of the tampon main bodies being radially arranged on the compression molding drum 101. During rotation of the compression molding drum 101, the absorbent body 21 is compressed in the diameter direction and shaped substantially into a cylinder.

Next, the absorbent body 21 shaped into a cylinder is heated by the heat drum 103. The temperature of the heat drum 103 is equal to or lower than 100 degrees and equal to or greater than 180 degrees, and preferably 110 degrees. Retaining mechanisms 104 of the heat drum 103 into which the tampon main body 20 is inserted are through-holes each having a cross-section substantially the same as that of the absorbent body 21, and are configured such that heat of the heat drum 103 is effectively transferred to the absorbent body 21. Furthermore, at that time, the absorbent body 21 is shaped into a bullet in which the front end is curved.

Next, the tampon main body 20 is transported to the assembly unit 105 while being cooled down. The assembly unit 105 is provided with a first conveyer 105a and a second conveyer 105b. The tampon main body 20 pushed out of the retaining mechanism 104 of the heat drum 103 is transported on the first conveyer 105a while maintaining its orientation. The second conveyer 105b is supplied with the applicator 30 produced in another line. At that time, the movable member 50 was inserted into the outer tube member 40, and as shown in FIG. 1A, the movable member 50 is positioned at the rear end side in the longitudinal direction of the outer tube member 40, and the stepped portion 45 of the outer tube member 40 and the catch section 51 of the movable member 50 are in contact with each other. Furthermore, the petalled part forming the front end opening 43 of the outer tube member 40 is spread out toward the outer circumferential side through the application of pressure.

Then, the tampon main body 20 on the first conveyer 105a is inserted rear end side first into the applicator 30 (into the outer tube member 40) on the second conveyer 105b. At that time, air is sucked from the rear end side of the movable member 50 such that the string 22 of the tampon main body 20 is moved first. Accordingly, the string 22 is pulled out from the opening at the rear end of the movable member 50 (i.e., the rear end of the applicator 30), and is exposed.

Next, the tampon 10 in which the tampon main body 20 is contained inside the outer tube member 40 is passed via an intermediate roller 106 to a front end molding unit 107. The front end molding unit 107 has the heating drum 107a, the cooling drum 107b, and front end mold sections (not shown) each having a hemispherical concavity.

On the heating drum 107a, the front end mold section (not shown) that has been heated is pressed toward the front end opening 43 of the outer tube member 40, and therefore the petalled part is curved inward (in the closing direction) and shaped into a dome. On the cooling drum 107b, the front end mold section (not shown) is pressed against the petalled part of the outer tube member 40 that has been heated and softened, and therefore the petalled part is cooled down and cured. As a result, as shown in FIG. 1A, the front end opening 43 is substantially closed in a state where the tampon main body 20 is contained in the outer tube member 40.

Next, the tampon main body 20 that has been inserted into the applicator 30 is supplied via an intermediate roller 106 to the string test unit 109. The string test unit 109 (corresponding to a test device) has string pulling units 110, a sensor 111, the rotating drum 108, and a controller (not shown). The plurality of string pulling units 110 are arranged along the circumferential direction of the rotating drum 108. The string pulling units 110 each retain the tampon 10 supplied from the intermediate roller 106. Note that the longitudinal direction of the tampon 10 matches the direction along a rotational shaft of the drum. Furthermore, the sensor 111 is positioned above the top of the rotating drum 108 (12 o'clock direction).

In the production line, a product in which the string 22 has not been properly attached to the absorbent body 21 of the tampon main body 20 also flows. Accordingly, the string test unit 109 performs a test (string tensile test) to check whether or not the string 22 has been properly attached to the absorbent body 21. Examples of the product in which the string 22 has not been properly attached to the absorbent body 21 include a product in which the string 22 was not sewn on the absorbent body 21 in the initial state due to a sewing needle coming off, a product in which the string 22 breaks and does not have a prescribed length due to the sewn string 22 being defective or due to the string 22 being damaged in subsequent processes, a product in which the string 22 is about to break, and a product in which the string 22 is about to detach from the absorbent body 21 due to the string 22 being loosely sewn on the absorbent body 21.

Thus, in the string test unit 109, in a state where a string holding section 125 holds the string 22 of the absorbent body 21 exposed from the rear end of the movable member 50, and tampon retaining sections 121a and 121b regulate movement of the absorbent body 21 via the applicator 30, the distance between the string holding section 125 and the tampon retaining sections 121a and 121b is increased in the longitudinal direction. Accordingly, a tensile force is applied to the string 22, thereby testing whether or not the string 22 has been properly attached to the absorbent body 21 (described later in detail).

Figure 4A:
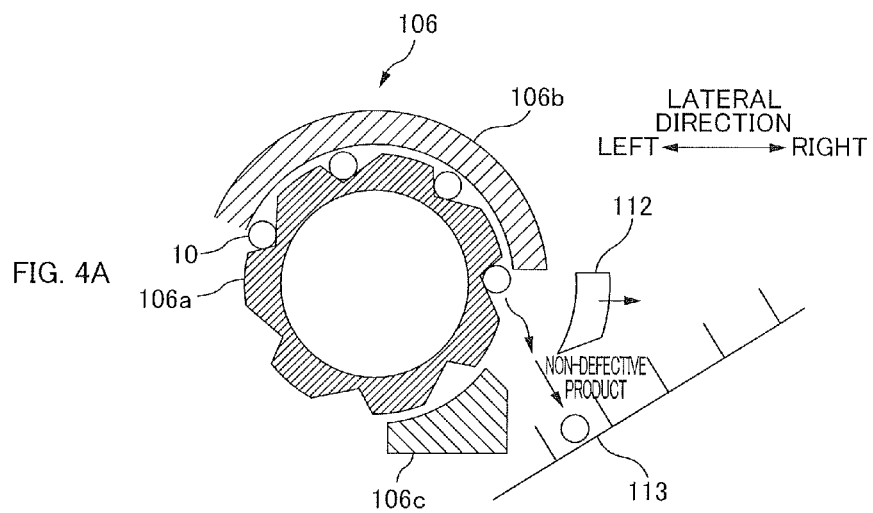
FIG. 4 shows schematic views of a defective product discharge section.
Figure 4B:
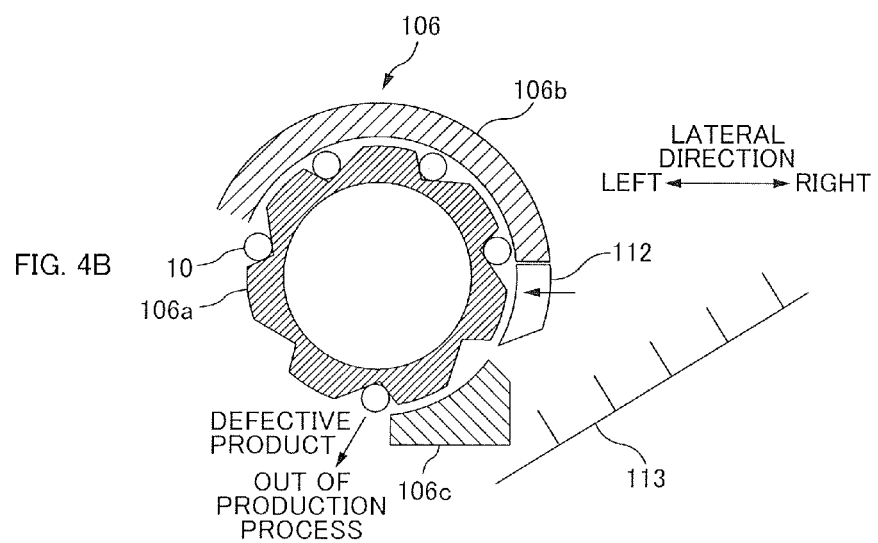

After the string tensile test, the tampon 10 reaches the defective product discharge section 112 via an intermediate roller 106. FIG. 4A shows the state in which the tampon 10 determined in the string tensile test as having a string 22 properly attached to the absorbent body 21 (non-defective product) is supplied to a transport belt 113, and FIG. 4B shows the state in which the tampon 10 determined in the string tensile test as having a string 22 improperly attached to the absorbent body 21 (defective product) is discharged out of the production process. The intermediate roller 106 has a rotational member 106a, and a first outer wall 106b and a second outer wall 106c which cover the outer circumference of the rotational member 106a. On the rotational member 106a, a plurality of grooves for containing the tampons 10 are arranged in the circumferential direction. In this example, the tampon 10 contained in the grooves of the rotational member 106a is not retained with a clamp or the like, and the tampon 10 is transported to the defective product discharge section 112 in a state where the tampon 10 is enclosed by the groove of the rotational member 106a and the first outer wall 106b.

The defective product discharge section 112 can cover a part of the outer circumferential face of the rotational member 106a between the first outer wall 106b and the second outer wall 106c. Accordingly, a side face on the intermediate roller 106 side of the defective product discharge section 112 is a face that is along the outer circumference of the rotational member 106a. Furthermore, the defective product discharge section 112 can move in a lateral direction, which is a direction that intersects the rotational shaft of the rotational member 106a. Accordingly, the defective product discharge section 112 can be positioned away from the first outer wall 106b and the second outer wall 106c such that the rotational member 106a and the defective product discharge section 112 are spaced away from each other as shown in FIG. 4A, and can be positioned between the first outer wall 106b and the second outer wall 106c as shown in FIG. 4B. The position in the lateral direction of the defective product discharge section 112 is controlled by the controller of the string test unit 109.

Assume that, as a result of the string tensile test performed on the tampon 10 retained by one of the string pulling units 110, the controller of the string test unit 109 determines that the string 22 has been properly attached to the absorbent body 21 in that tampon 10. In this case, when the tampon 10 reaches the defective product discharge section 112, the controller moves the defective product discharge section 112 away from the first outer wall 106b and the second outer wall 106c such that the rotational member 106a and the defective product discharge section 112 are spaced away from each other as shown in FIG. 4A. As a result, there is nothing that holds the tampon 10 against the outer circumferential face side of the rotational member 106, and the tampon 10 falls on the transport belt 113. The tampon 10 on the transport belt 113 is transported to subsequent processes (e.g., wrapping process).

On the other hand, assume that, as a result of the string tensile test performed on the tampon 10 retained by one of the string pulling units 110, the controller of the string test unit 109 determines that the string 22 has not been properly attached to the absorbent body 21 in that tampon 10. In this case, when the tampon 10 reaches the defective product discharge section 112, the controller places the defective product discharge section 112 between the first outer wall 106b and the second outer wall 106c as shown in FIG. 4B. As a result, the tampon 10 is enclosed by the groove of the rotational member 106a and the defective product discharge section 112 even after moving away from the first outer wall 106b, and therefore the tampon 10 does not fall on the transport belt 113 and reaches the second outer wall 106c. On the downstream side of the second outer wall 106c, there is nothing that covers the outer face of the rotational member 106a, and the tampon 10 moves away from the rotational member 106a and is discharged out of the production process.

That is to say, based on a result of the string tensile test performed on a given tampon 10, the controller of the string test unit 109 controls the position in the lateral direction of the defective product discharge section 112 at a point in time when the tampon 10 reaches the defective product discharge section 112. Then, the controller supplies a product that passed the string tensile test (non-defective product) to the transport belt 113 leading to subsequent processes, and discharges a product that did not pass the string tensile test (defective product) out of the production process. As a result, it is possible to produce and provide the tampon 10 in which the string 22 has been properly attached to the absorbent body 21.

Accordingly, the controller of the string test unit 109 calculates the point in time when a given tampon having undergone the string tensile test reaches the defective product discharge section 112. For example, the controller calculates the period of time after when a given tampon 10 undergoes the string tensile test to when that tampon 10 reaches the defective product discharge section 112. It is possible to calculate this period of time based on the transport distance from a location where the tampon 10 opposes the sensor 111 of the string test unit 109 shown in FIG. 2 to a location where the tampon 10 reaches the defective product discharge section 112, and the transport speed of the tampon 10 in the tampon producing apparatus 100.

In this example, the tampon 10 that did not pass the string tensile test is discharged out of the production process by controlling the position in the lateral direction of the defective product discharge section 112, but there is no limitation to this. For example, the product that did not pass the test may be discharged out of the production process at a point in time when a clamp placed from one end to the other end of a groove of the intermediate roller 106 is released. The tampon 10 supplied to the intermediate roller 106 is retained with a clamp. In the case of the tampon 10 in which the string 22 has been properly attached, the clamp is released at a point in time when the tampon 10 reaches the transport belt 113. On the other hand, in the case of the tampon 10 in which the string 22 has not been properly attached, the clamp is not released at a point in time when the tampon 10 reaches the transport belt 113, but is released at a point in time when that tampon 10 is discharged out of the production process. As a result, it is possible to classify the tampons 10 in which the string 22 has been properly attached and the tampons 10 in which the string 22 has not been properly attached.

String Tensile Test

<String Pulling Unit 110>

Figure 5A:
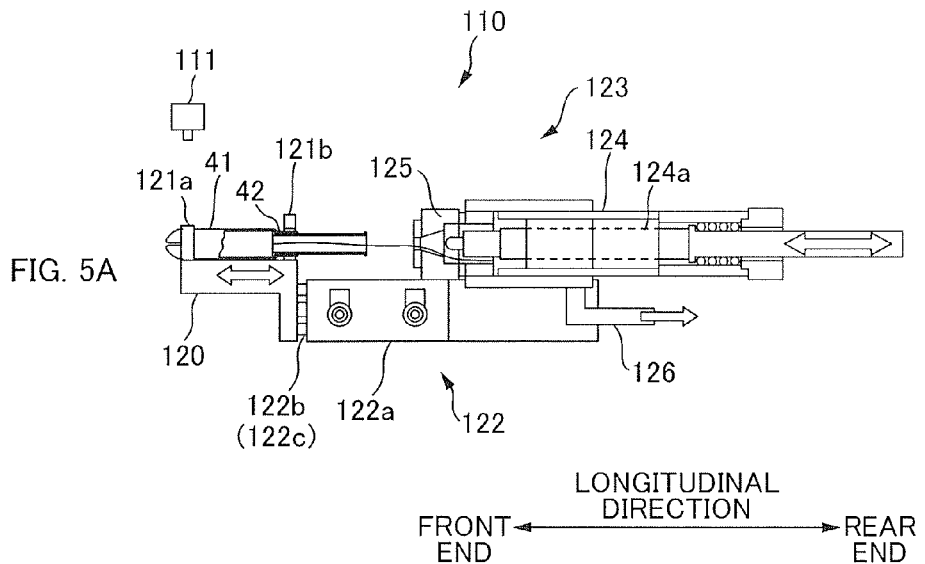
FIGS. 5A and 5B show views illustrating a string pulling unit.
Figure 5B:
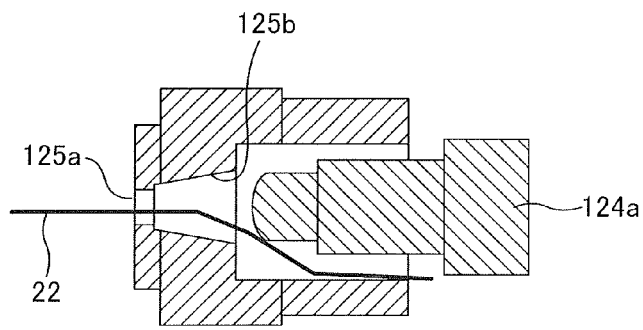
Figure 5B:
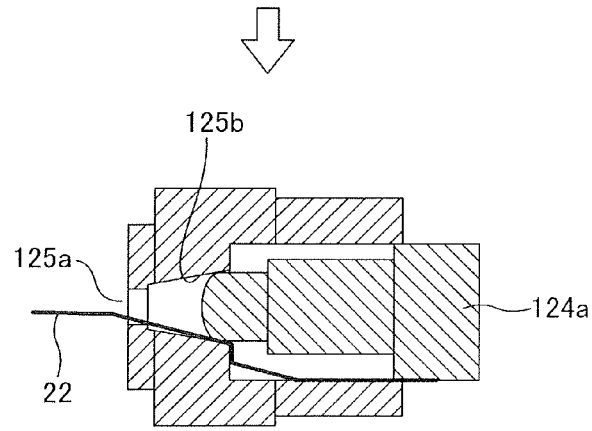

FIGS. 5A and 5B show views illustrating the string pulling unit 110. The string pulling unit 110 has a retaining table 120, the tampon retaining sections 121a and 121b (corresponding to regulation sections) that regulate movement of the absorbent body 21 via the applicator 30, a movable air cylinder 122, and a string holding mechanism 123. The tampon 10 is disposed on the retaining table 120, and the tampon retaining sections 121a and 121b are arranged on the upper face of the retaining table 120. The retaining table 120 is disposed at the front end of a piston rod 122b included in the movable air cylinder 122. Accordingly, the retaining table 120 can move in the longitudinal direction together with the tampon 10 (the applicator 30) that is retained by the tampon retaining sections 121a and 121b.

The movable air cylinder 122 has a main body section 122a that is provided with a cylinder tube, and a piston unit 122c in which a piston capable of moving inside the cylinder tube and the piston rod 122b are unitarily formed. The piston rod 122b links the retaining table 120 and the piston. The main body section 122a is fixed to the rotating drum 108 (see FIG. 2) and rotates together with the rotating drum 108. Furthermore, the string holding mechanism 123 is also attached to the main body section 122a.

The string holding mechanism 123 has a string holding air cylinder 124, the string holding section 125 (corresponding to a holding section), and a suction section 126. The string holding air cylinder 124 has a rod section 124a, and the rod section 124a can move in the longitudinal direction. Furthermore, the string holding section 125 is disposed at the front end section of the rod section 124a.

FIG. 5B shows enlarged views of the string holding section 125. The string holding section 125 is provided with a hole 125a. The hole 125a has a funnel section 125b that becomes wider from the outer side to the inner side. In an ordinary state (the lower view in FIG. 5B), the rod section 124a of the string holding air cylinder 124 is biased to the front end side in the longitudinal direction by a coiled spring, so that the front end of the rod section 124a is pressed against the funnel section 125b and blocks the hole 125a. On the other hand, when air inside the cylinder tube of the string holding air cylinder 124 is sucked, the rod section 124a is pulled to the rear end side in the longitudinal direction (the upper view in FIG. 5B), so that the hole 125a and the rod section 124a are spaced apart. Note that the string holding mechanism 123 is disposed at the rear end side of the tampon 10 that is supported by the retaining table 120, and the center lines of the tampon main body 20 and the hole 125a are arranged so as to be on a substantially straight line.

<Test Method>

In the production process shown in FIG. 2, after the front end molding unit 107, the tampon 10 is passed via the intermediate roller 106 to the retaining table 120 of the string pulling unit 110. At that time, air is not supplied to the movable air cylinder 122. Accordingly, the piston rod 122b is not extended, and, as shown in FIG. 5A, the retaining table 120 and the main body section 122a are positioned relatively close to each other. When the tampon 10 is passed to the retaining table 120, the clamp of the tampon retaining section 121b on the rear end side is closed, and the tampon 10 is retained. At that time, the tampon main body 20 is contained inside the outer tube member 40, and, as shown in FIG. 1A, the movable member 50 is projected to the rear end side with respect to the outer tube member 40. Accordingly, the rear end of the movable member 50 is positioned relatively close to the hole 125a of the string holding section 125.

When the tampon 10 is retained on the retaining table 120, the rod section 124a of the string holding air cylinder 124 is pulled to the rear end side in the longitudinal direction, and the hole 125a and the front end of the rod section 124a are spaced apart (the upper view in FIG. 5B). In this state, air is sucked by the suction section 126, so that air is sucked from the gap between the funnel section 125b and the rod section 124a. As a result, the rear end of the string 22 of the tampon 10 is guided from the hole 125a of the string holding section 125 into the gap between the funnel section 125b and the rod section 124a (the upper view in FIG. 5B). Subsequently, air suction by the suction section 126 is stopped, the rod section 124a is biased by the coiled spring to the front end side in the longitudinal direction, and the front end of the rod section 124a is pressed against the funnel section 125b (the lower view in FIG. 5B). As a result, the string 22 is held between the rod section 124a and the funnel section 125b, that is, the string 22 is held by the string holding section 125.

When the string 22 is held by the string holding section 125 while air is sucked by the suction section 126 from the rear end side of the absorbent body 21 in this manner, the string holding section 125 can hold the string 22 while suppressing slack in the string. Furthermore, if air is sucked by the suction section 126, the string 22 not exposed from the movable member can be exposed from the movable member 50, and therefore the string 22 can be held by the string holding section 125.

While the string holding mechanism 123 is holding the string 22, the rotating drum 108 of the string test unit 109 continues to rotate. Then, before the tampon 10 retained on the retaining table 120 opposes the sensor 111, air is supplied to the movable air cylinder 122, and a force that extends the piston rod 122b to the front end side in the longitudinal direction acts on the piston rod 122b. As a result, a force that causes movement to the front end side in the longitudinal direction acts also on the retaining table 120 and the tampon 10 (the outer tube member 40) retained on the retaining table 120. Note that, since the string 22 of the tampon 10 retained on the retaining table 120 is held by the string holding section 125, if the string 22 has been properly attached to the absorbent body 21, a tensile force acts on the string 22, and a force that suppresses the movement of the retaining table 120 acts.

In other words, as a result of increasing the distance in the longitudinal direction between the tampon retaining sections 121a and 121b that regulate movement of the absorbent body 21 on the retaining table 120 and the string holding section 125, thereby applying a tensile force to the string 22, the movement of the retaining table 120 is suppressed. In this embodiment, the distance in the longitudinal direction between the string holding section 125 and the tampon retaining sections 121a and 121b is increased by moving the tampon retaining sections 121a and 121b (movable sections) that can move in the longitudinal direction to the front end side in the longitudinal direction with respect to the string holding section 125 (corresponding to a fixed section) whose position in the longitudinal direction is fixed.

Specifically, the tampon retaining sections 121a and 121b shown in FIG. 5A are each configured by a pair of protruding sections, and the tampon 10 is disposed between the protruding sections, and therefore movement of the tampon 10 is regulated. In the tampon retaining section 121a on the front end side, the large-diameter section 41 of the outer tube member 40 is positioned between the pair of protruding sections, and, in the tampon retaining section 121b on the rear end side, the small-diameter section 42 of the outer tube member 40 is positioned between the pair of protruding sections. Furthermore, a releasable clamp placed over the protruding sections is disposed at the tampon retaining section 121b on the rear end side. In this manner, the tampon retaining sections 121a and 121b regulate the movement of the outer tube member 40 on the retaining table 120. Furthermore, as shown in FIG. 1A, the front end of the movable member 50 is formed as the catch section 51 having an outer diameter larger than the inner diameter of the small-diameter section 42 of the outer tube member 40. Thus, the movable member 50 is configured so as not to be detached from the rear end side in the longitudinal direction of the outer tube member 40. Accordingly, the tampon retaining sections 121a and 121b also restrict the movement of the inner tube member 50 to the rear end side in the longitudinal direction. Inside the outer tube member 40, the absorbent body 21 is in contact with an end face on the front end side of the movable member 50. Accordingly, a tensile force acts on the string 22 attached to the absorbent body 21, and even when a force that moves the absorbent body 21 to the rear end side in the longitudinal direction acts, the movement of the absorbent body 21 to the rear end side in the longitudinal direction is regulated by the tampon retaining sections 121a and 121b via the front end face of the movable member 50. Furthermore, in the tampon 10 of this embodiment, as shown in FIG. 1A, the outer diameter of the absorbent body 21 is larger than the inner diameter of the small-diameter section 42 of the outer tube member 40, which also allows a tensile force to act on the string 22, and therefore the absorbent body 21 cannot be moved to the rear end side in the longitudinal direction inside the outer tube member 40 even when a force that moves the absorbent body 21 to the rear end side in the longitudinal direction acts.

Furthermore, the distance between the pair of protruding sections of the tampon retaining section 121b on the rear end side is larger than the outer diameter of the small-diameter section 42 of the outer tube member 40 and is smaller than the outer diameter of the large-diameter section 41. Accordingly, a tensile force acts on the string 22 attached to the absorbent body 21, and, even when a force that moves the outer tube member 40 to the rear end side in the longitudinal direction acts, the rear end of the large-diameter section 41 of the outer tube member 40 is brought into contact with the tampon retaining section 121b on the rear end side, and the movement of the outer tube member 40 to the rear end side in the longitudinal direction can be reliably regulated. That is to say, even when a force that moves the outer tube member 40 to the rear end side in the longitudinal direction acts, the tampon retaining sections 121a and 121b can regulate the movement of the outer tube member 40 without slipping, and can apply a predetermined tensile force to the string 22.

As a result of a predetermined tensile force applied to the string 22, for example, in the case that the string 22 breaks, or in the case that the string 22 is detached from the absorbent body 21, it can be determined that the string 22 has not been properly attached to the absorbent body 21. Otherwise, it can be determined that the string 22 has been properly attached to the absorbent body 21 (described later in detail).

Note that a force applied to the piston rod 122b of the movable air cylinder 122 may be adjusted such that the tensile force applied to the string 22 is greater than 20 N and less than 100 N, and preferably 60 N. The reason for this is that, if the force applied to the string 22 is 20 N or less, that force may be less than the force applied to the string 22 (resisting force) when removing the tampon main body 20 out of the vaginal cavity, and, if the force applied to the string 22 is 100 N or greater, the absorbent body 21 may be damaged.

Furthermore, in this embodiment, the tampon retaining sections 121a and 121b (regulation sections) regulate the movement of the outer tube member 40, thereby regulating the movement of the absorbent body 21, but there is no limitation to this. For example, the tampon retaining sections may regulate the movement in the longitudinal direction of the movable member 50 (inner tube). Also in this case, the rear end of the absorbent body 21 and the front end face of the movable member 50 are brought into contact with each other, and therefore the movement of the absorbent body 21 to the rear end side in the longitudinal direction can be regulated when a tensile force acts on the string 22. As a result, a predetermined tensile force can be applied to the string 22 of the absorbent body 21. Furthermore, in the case of a tampon having a configuration in which the movable member 50 is detached from the rear end side of the outer tube member 40, the tampon retaining sections 121a and 121b regulate the movement in the longitudinal direction of the movable member 50 (inner tube), and therefore the movement of the absorbent body 21 to the rear end side in the longitudinal direction can be regulated.

<Test Result>

FIGS. 6A to 6C show views illustrating a test result in a case where the string 22 is held by the string holding section 125 without slack, and the string 22 has been properly attached to the absorbent body 21 of the tampon main body 20. FIG. 6A is a view showing a state after the string 22 is held by the string holding section 125 without slack. At that time, air is not supplied to the movable air cylinder 122, and a force that causes movement to the front end side in the longitudinal direction does not act on the retaining table 120 and the absorbent body 21 (the outer tube member 40). At that time, the distance in the longitudinal direction from the hole 125a of the string holding section 125 to the middle portion of the tampon retaining section 121a is a "distance L".

Subsequently, as shown in FIG. 6B, air is supplied to the movable air cylinder 122, and a force that causes movement to the front end side in the longitudinal direction acts on the retaining table 120 and the absorbent body 21. However, the string 22 has been properly attached to the absorbent body 21, and the string 22 is held by the string holding section 125 without slack. Accordingly, when moving the retaining table 120 and the absorbent body 21 to the front end side in the longitudinal direction, the string 22 is tensioned, and the retaining table 120 and the absorbent body 21 move to the front end side in the longitudinal direction slightly (by Δ1). That is to say, the distance from the hole 125a of the string holding section 125 to the middle section of the tampon retaining section 121a is hardly changed, and that distance becomes "distance L+Δ1". That is to say, as a result of increasing the distance between the tampon retaining sections 121a and 121b and the string holding section 125, the amount of change in the distance becomes a slight amount Δ1.

At the time of the test, the sensor 111 is positioned at a location that is off the hole 125a of the string holding section 125 toward the front end side in the longitudinal direction by the "distance L (corresponding to a predetermined distance)". Accordingly, before the tensile force is applied to the string 22 (the state in FIG. 6A), the tampon retaining section 121a is positioned at a location where it is detected by the sensor 111. Specifically, before the tensile force is applied to the string 22, the sensor 111 is positioned at a location where it opposes the middle portion in the longitudinal direction of the tampon retaining section 121a. Then, after the tensile force is applied to the string 22, the distance of the absorbent body 21 moved in the longitudinal with respect to the string holding section 125 is a slight amount, and therefore the tampon retaining section 121a continues to be positioned at a location where it is detected by the sensor 111. Specifically, as shown in FIGS. 6B and 6C, even after the tensile force is applied to the string 22, the sensor 111 is positioned at a location where it opposes substantially the middle portion in the longitudinal direction of the tampon retaining section 121a, and the sensor 111 can detect the tampon retaining section 121a.

It is assumed that the sensor 111 is an optical sensor. An optical sensor emits light, and detects the existence or absence of an object on an optical path of the emitted light based on whether or not the emitted light is blocked. Furthermore, the height of the outer tube member 40 of the tampon 10 in a direction that intersects the longitudinal direction is greater than the height of the tampon retaining section 121a. The focus of the sensor 111 is set at the height of the tampon retaining section 121a. Accordingly, the sensor 111 can detect that there is the tampon retaining section 121a when the sensor 111 opposes the tampon retaining section 121a.

The controller of the string test unit 109 acquires a detection result of the sensor 111 when the sensor 111 opposes the tampon 10 retained by the string pulling unit 110 that is rotated by the rotating drum 108. In the case that the sensor 111 detects the tampon retaining section 121a, the controller determines that the string 22 has been properly attached to the absorbent body 21 in the tampon 10 retained by that string pulling unit 110.

Figure 7A:
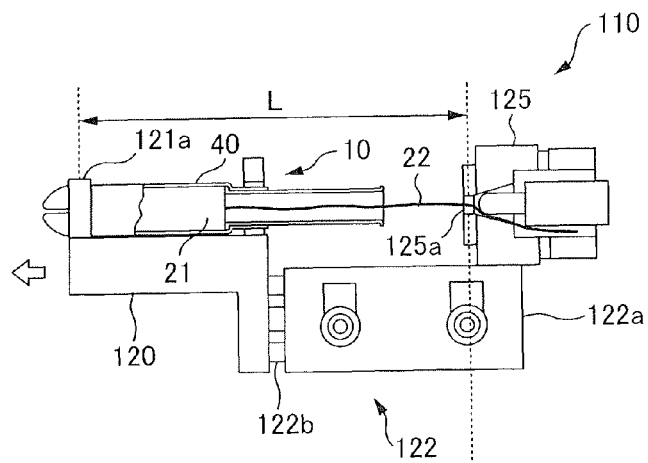
FIGS. 7A to 7C show views illustrating a test result in a case where a string has been properly attached to an absorbent body.
Figure 7B:
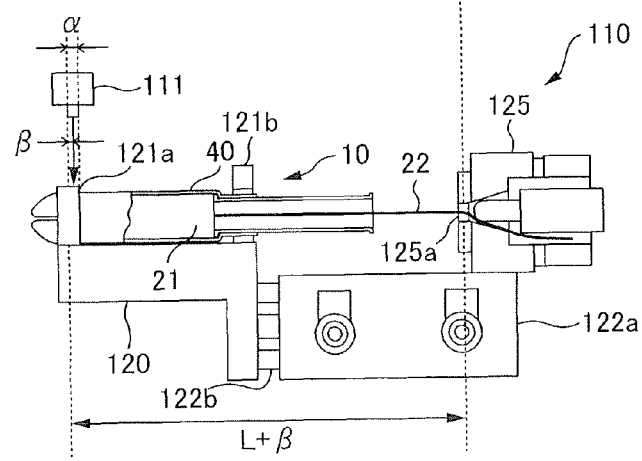
Figure 7C:
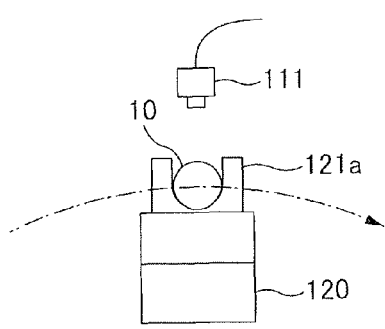

FIGS. 7A to 7C show views illustrating a test result in a case where the string 22 has been properly attached to the absorbent body 21, but the string 22 is held by the string holding section 125 with slack. FIG. 7A is a view showing the state in which the string 22 is held by the string holding section 125 with slack in the string 22, where a force that causes movement to the front end side in the longitudinal direction does not yet act on the retaining table 120 and the absorbent body 21. At that time, the distance in the longitudinal direction from the hole 125a of the string holding section 125 to the middle portion of the tampon retaining section 121a is the "distance L" as in the case of FIG. 6A described above. That is to say, before the distance between the tampon retaining sections 121a and 121b and the string holding section 125 is increased, the tampon retaining section 121a is positioned at a location where it is detected by the sensor 111.

Subsequently, as shown in FIG. 7B, air is supplied to the movable air cylinder 122, and a force that causes movement to the front end side in the longitudinal direction acts on the retaining table 120 and the absorbent body 21. As a result, the string 22 with slack is tensioned, and the retaining table 120 and the absorbent body 21 move to the front end side in the longitudinal direction by a distance β (actually approximately 2 to 3 mm). However, since the string 22 has been properly attached to the absorbent body 21, the retaining table 120 and the absorbent body 21 move to the front end side in the longitudinal direction by the amount of slack in the string 22 (by the distance β), but does not move any further. As a result, as shown in FIG. 7B, the distance in the longitudinal direction from the hole 125a of the string holding section 125 to the middle section of the tampon retaining section 121a becomes the "distance L+β". That is to say, as a result of increasing the distance between the tampon retaining sections 121a and 121b and the string holding section 125, the amount of change in the distance becomes "β".

The distance in the longitudinal direction from the sensor 111 to the hole 125a of the string holding section 125 is set to the "distance L". Accordingly, in the case that the absorbent body 21 moves to the front end side in the longitudinal direction by the distance β with respect to the string holding section 125, as shown in FIG. 7B, the sensor 111 opposes a position that is off the middle section of the tampon retaining section 121a toward the rear end side in the longitudinal direction by the distance β. As a result, as shown in FIGS. 7B and 7C, even after the tensile force is applied to the string 22, the tampon retaining section 121a is positioned at a location where it is detected by the sensor 111, and the controller determines that the string 22 has been properly attached to the absorbent body 21.

In this manner, the string 22 may be held by the string holding section 125 with slack in the string 22. Accordingly, even when the string 22 has been properly attached, the retaining table 120 and the absorbent body 21 move to the front end side in the longitudinal direction by the amount of slack in the string 22. The tampon retaining section 121a is provided with a predetermined width in the longitudinal direction such that the sensor 111 can detect the tampon retaining section 121a even in that case.

It is assumed that, in this example, the width in the longitudinal direction of the tampon retaining section 121a is "2a". In the case that the distance of the retaining table 120 and the absorbent body 21 moved by the movable air cylinder 122 is slight as shown in FIG. 6B described above, the sensor 111 opposes substantially the middle portion of the tampon retaining section 121a. On the other hand, in the case that the retaining table 120 and the absorbent body 21 are moved by the movable air cylinder 122 to the front end side in the longitudinal direction by the amount of slack in the string, the sensor 111 opposes a position that is off the middle portion of the tampon retaining section 121a toward the rear end side by the distance of the absorbent body 21 moved (by β in FIG. 7B). Thus, a distance α from the middle portion of the tampon retaining section 121a to the rear end is made greater than the distance (β in the drawing) by which the retaining table 120 and the absorbent body 21 may be moved by the movable air cylinder 122 when the string 22 is held with slack. Accordingly, the sensor 111 can detect the tampon retaining section 121a, and the controller can determine that the string 22 has been properly attached to the absorbent body 21.

Figure 8A:
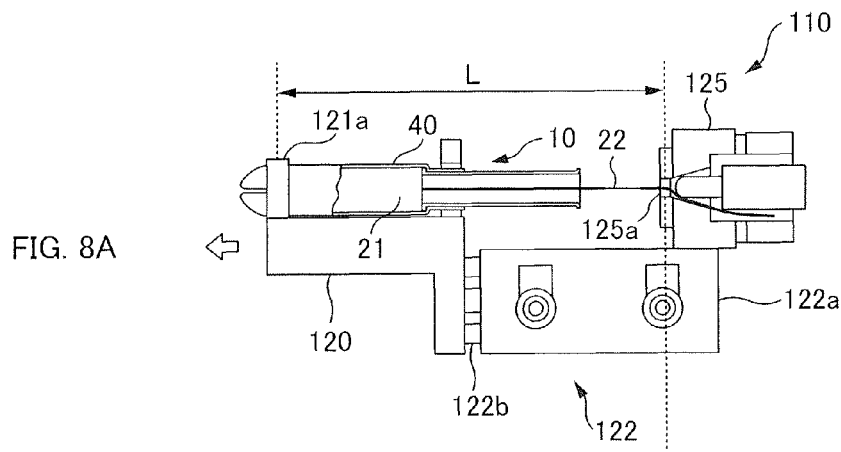
FIGS. 8A to 8C show views illustrating a test result in a case where a string has not been properly attached to an absorbent body.
Figure 8B:
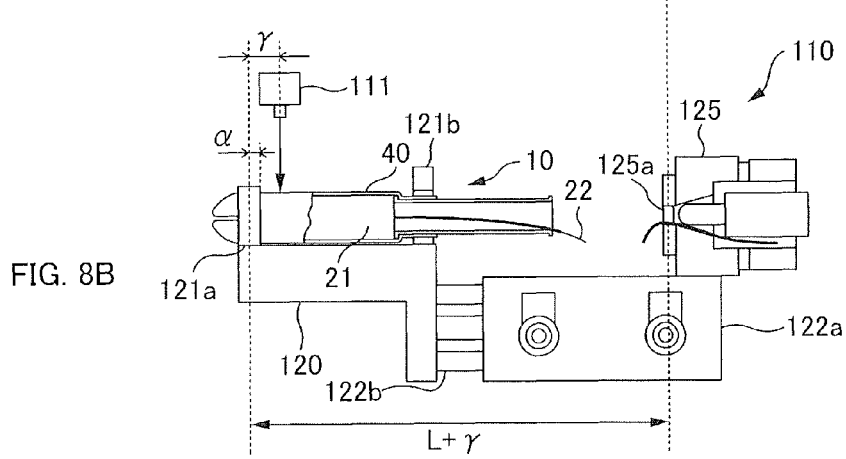
Figure 8C:
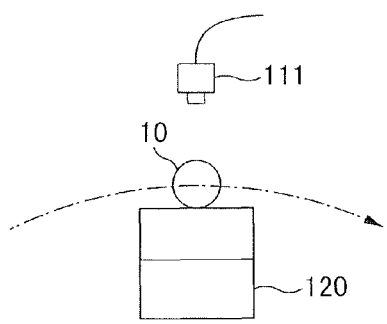

FIGS. 8A to 8C show views illustrating a test result in a case where the string 22 attached to the absorbent body 21 is easy to break, that is, the string 22 has not been properly attached to the absorbent body 21. The string 22 is easy to break, for example, because the string 22 in the initial state is defective, or the string 22 is damaged in the production process. In this case, as a result of supplying air to the movable air cylinder 122, allowing a force that causes movement to the front end side in the longitudinal direction to act on the retaining table 120 and the absorbent body 21, and applying a tensile force to the string 22, the string 22 breaks. Furthermore, in the case that the string 22 is loosely sewn on the absorbent body 21, the string 22 is detached from the absorbent body 21. That is to say, in the case that the string 22 cannot withstand the tensile strength of the force by which the piston rod 122b of the movable air cylinder 122 presses against the retaining table 120 (e.g., 60 N), the string 22 breaks or is detached from the absorbent body 21. In this case, the force that moves the retaining table 120 due to the pressing operation by the piston rod 122b cannot be suppressed by the tensile force that acts on the string 22, and the retaining table 120 moves to the front end side in the longitudinal direction. Accordingly, the absorbent body 21 retained on the retaining table 120 also moves to the front end side in the longitudinal direction.

In this case, although the distance in the longitudinal direction from the hole 125a of the string holding section 125 to the middle portion of the tampon retaining section 121a is the "distance L" as shown in FIG. 8A before the distance between the tampon retaining sections 121a and 121b and the string holding section 125 is increased, the distance is the "distance L+γ" as shown in FIG. 8B after the distance is increased. That is to say, the amount of change in the distance between the tampon retaining section 121a and the string holding section 125 becomes "γ".

The amount γ of change in the distance (actually approximately several centimeters) is greater than the distance (β in FIG. 7B) of the retaining table 120 and the absorbent body moved when the string 22 is held with slack, and is greater than the distance α from the middle portion of the tampon retaining section 121a to the rear end section. Accordingly, although the tampon retaining section 121a is positioned at a location where it is detected by the sensor 111 before the distance between the tampon retaining sections 121a and 121b and the string holding section 125 is increased, after the distance is increased, as shown in FIGS. 8B and 8C, the tampon retaining section 121a is not positioned at a location where it is detected by the sensor 111, and the sensor 111 opposes the outer tube member 40 of the tampon 10. The focus of the sensor 111 is set at the height of the tampon retaining section 121a, which is greater than that of the outer tube member 40 of the tampon 10. Accordingly, when the sensor 111 opposes the outer tube member 40 of the tampon 10, the sensor 111 detects no object. In the case that the sensor 111 does not detect the tampon retaining section 121a and detects no object, the controller of the string test unit 109 can determine that the string 22 has not been properly attached to the absorbent body 21.

In the case that the string 22 breaks or the like as a result of allowing a force that causes movement to the front end side in the longitudinal direction to act on the retaining table 120 and the absorbent body 21 and applying a tensile force to the string 22 in this manner, the sensor 111 is set so as to oppose not the tampon retaining section 121a but the outer tube member 40. Thus, the distance α from the middle section of the tampon retaining section 121a to the rear end is made less than the distance (γ in the drawing) by which the retaining table 120 and the absorbent body 21 are moved by the movable air cylinder 122 when the string 22 breaks or is detached from the absorbent body 21. Conversely, the amount of the piston rod 122b of the movable air cylinder 122 extended is adjusted such that the amount γ of the retaining table 120 moved when the string 22 breaks or the like is greater than the distance α from the middle section of the tampon retaining section 121 to the rear end section. Accordingly, when the string 22 breaks or is detached from the absorbent body 21 as a result of applying a tensile force to the string 22, the sensor 111 opposes the outer tube member 40, and the controller can determine that the string 22 has not been properly attached to the absorbent body 21.

FIGS. 9A to 9C show views illustrating a test result in a case where the string 22 has not been attached to the absorbent body 21. In the case that the string 22 has not been attached to the absorbent body 21, even when the string holding section 125 tries to hold the string 22, the string 22 cannot be held. In a similar manner, also when the string 22 having a length less than the prescribed length is attached to the absorbent body 21 or when the string 22 breaks before the string tensile test, the string 22 cannot be held by the string holding section 125. Furthermore, the string 22 may be tucked up inside the movable member 50. In the string holding mechanism 123, air is sucked from the hole 125a of the string holding section 125, and therefore the string 22 is guided into a position between the hole 125a and the funnel section 125b. Thus, air suction from the hole 125a cancels tucking up of the string 22, and therefore the string 22 may be held by the string holding section 125.

In the case that the string 22 cannot be held by the string holding section 125 in this manner, when air is supplied to the movable air cylinder 122, and a force that causes movement to the front end side in the longitudinal direction acts on the retaining table 120 and the absorbent body 21, the movement force cannot be suppressed by the tensile force of the string 22. As a result, the retaining table 120 and the absorbent body 21 freely move to the front end side in the longitudinal direction with respect to the string holding section 125 by the length γ of the piston rod 122b of the movable air cylinder 122 extended. That is to say, as a result of increasing the distance between the tampon retaining sections 121a and 121b and the string holding section 125, the amount of change in the distance becomes "γ".

Thus, although the tampon retaining section 121a is positioned at a location where it is detected by the sensor 111 before the distance between the tampon retaining sections 121a and 121b and the string holding section 125 is increased, after the distance is increased, as shown in FIGS. 9B and 9C, the tampon retaining section 121a is not positioned at a location where it is detected by the sensor 111. The sensor 111 opposes the outer tube member 40 of the tampon 10 and detects no object. Accordingly, based on the fact that the sensor 111 detects no object, the controller of the string test unit 109 determines that the string 22 has not been properly attached to the absorbent body 21.

In summary, in the string tensile test, the rear end of the string 22 exposed from the applicator 30 retained on the retaining table 120 is held by the string holding section 125, and a force that causes movement to the front end side in the longitudinal direction (to the side away from the string holding section 125) is applied to the retaining table 120 and the absorbent body 21. That is to say, the distance between the tampon retaining sections 121a and 121b and the string holding section 125 is increased.

As a result, when the string 22 is held by the string holding section 125, and the string 22 has been properly attached to the absorbent body 21, a tensile force acts on the string 22, and movement of the retaining table 120 and the absorbent body 21 is suppressed. Thus, the amount of change in the distance between the tampon retaining sections 121a and 121b and the string holding section 125 is larger than zero (the slight amount Δ1 in FIG. 6 or more), and is smaller than the length of slack in the string 22 extended (β in FIG. 7) or less.

On the other hand, when the string 22 cannot be held by the string holding section 125 due to the length of the string 22 being short or when the string 22 is about to break, movement of the retaining table 120 and the absorbent body 21 cannot be suppressed by the tensile force of the string 22. Thus, the amount of change in the distance between the tampon retaining sections 121a and 121b and the string holding section 125 corresponds to the extended amount of the piston rod 122b that presses against the retaining table 120 (γ in FIGS. 8 and 9).

In this manner, it is determined whether or not the string 22 has been properly attached to the absorbent body 21 based on the amount of change in the distance in the longitudinal direction between the tampon retaining sections 121a and 121b and the string holding section 125 before and after increasing the distance between the tampon retaining sections 121 and the string holding section 125. Accordingly, it can be determined whether or not the string 22 having the prescribed length has been attached to the absorbent body 21 and whether or not the string 22 can withstand the predetermined tensile strength (the force of the piston rod 122b pressing against the retaining table 120, the resistance when the tampon main body 20 is detached). Specifically, if the amount of change in the distance between the tampon retaining sections 121a and 121b and the string holding section 125 is a threshold value or less, it can be determined that the string 22 can withstand the predetermined tensile strength and that the string 22 has been properly attached. On the other hand, if the amount of change in the distance between the tampon retaining sections 121a and 121b and the string holding section 125 is greater than the threshold value, it can be determined that the string 22 breaks or is detached from the absorbent body 21 because the string 22 cannot withstand the predetermined tensile strength.

In this embodiment, it is determined whether or not the string 22 has been properly attached to the absorbent body 21 based on whether or not the sensor 111 detects the tampon retaining section 121a. Then, the tampon 10 determined as having a string 22 properly attached to the absorbent body 21 is supplied to the transport belt 113 leading to subsequent processes as shown in FIG. 4A, and the tampon 10 determined as having a string 22 improperly attached to the absorbent body 21 is discharged out of the production process as shown in FIG. 4B.

Note that the test may be performed by increasing the distance between the tampon retaining sections 121a and 121b and the string holding section 125, thereby applying a tensile force to the string 22, but the method is not limited to those for determining whether or not the string 22 has been properly attached based on the existence or absence of the tampon retaining section 121a detected by the sensor 111. For example, visual inspections may be used to check whether or not the string 22 breaks or whether or not the string 22 is detached from the absorbent body 21.

Furthermore, the sensor 111 may be positioned at a location where it opposes the tampon retaining section 121b on the rear end side before the distance between the tampon retaining sections 121a and 121b and the string holding section 125 is increased. In this case, it can be determined whether or not the string 22 has been properly attached based on the existence or absence of the tampon retaining section 121b on the rear end side after the distance is increased. Furthermore, the position of the sensor 111 may be adjusted such that, if the string 22 has been properly attached, the sensor 111 is positioned at a location where it does not detect the tampon 10 before and after increasing the distance between the tampon retaining sections 121a and 121b and the string holding section 125, and such that, if there is an attachment failure of the string 22 after the distance is increased, the sensor 111 is positioned at a location where it detects the tampon 10.

Furthermore, it may be determined whether or not the string 22 has been properly attached, by actually detecting the difference between the position of the tampon retaining sections 121a and 121b before the distance between the tampon retaining sections 121a and 121b and the string holding section 125 is increased and the position of the tampon retaining sections 121a and 121b after the distance is increased, and calculating the amount of change in the distance.

Furthermore, in this embodiment, a force that moves the retaining table 120 (the tampon retaining sections 121a and 121b and the absorbent body 21) to the front end side in the longitudinal direction with respect to the string holding section 125 is applied, but there is no limitation to this. For example, a force that moves the string holding section 125 to the rear end side in the longitudinal direction with respect to the retaining table 120 (the tampon retaining sections 121a and 121b) may be applied. In this case, the tampon retaining sections 121a and 121b correspond to fixed sections, and the string holding section 125 corresponds to a movable section. Accordingly, the sensor 111 may be positioned at a location where the sensor 111 detects the string holding section 125 before the distance between the tampon retaining sections 121a and 121b and the string holding section 125 is increased, and it may be determined whether or not the string 22 has been properly attached based on whether or not the sensor 111 detects the string holding section 125 after the distance is increased.

Other String Tensile Test

Figure 10A:
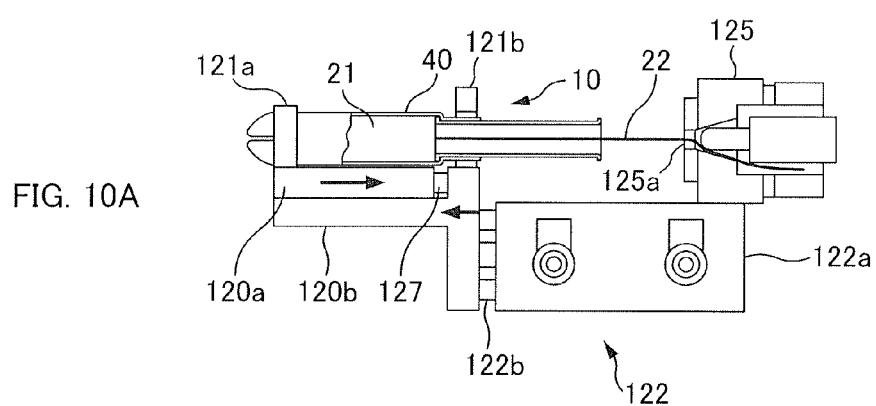
FIGS. 10A and 10B show views illustrating another string tensile test.
Figure 10B:
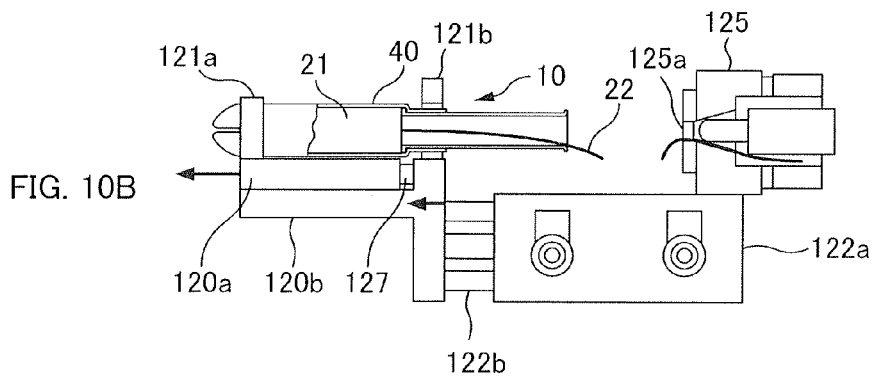

FIGS. 10A and 10B show views illustrating another string tensile test. In the above-described string tensile test, it is determined whether or not the string 22 has been properly attached to the absorbent body 21 based on the amount of relative movement in the longitudinal direction between the string holding section 125 and the absorbent body 21 as a result of applying a force in a direction that increases the distance in the longitudinal direction between the string holding section 125 and the absorbent body 21, but there is no limitation to this. In the example shown in FIG. 10, the retaining table 120 is divided into a first retaining table 120a that retains the tampon 10 and a second retaining table 120b that is linked to the piston rod 122b of the movable air cylinder 122. The first retaining table 120a can move in the longitudinal direction with respect to the second retaining table 120b. Furthermore, a load cell 127 that detects a compressive force is provided between the first retaining table 120a and the second retaining table 120b.

As in the foregoing embodiment, after the string 22 is held from the rear end by the string holding section 125, air is supplied to the movable air cylinder 122. Accordingly, a force that moves the first retaining table 120a to the front end side in the longitudinal direction is applied from the second retaining table 120b via the load cell 127 to the first retaining table 120a. However, in the case that the string 22 has been properly attached to the absorbent body 21 (FIG. 10A), a tensile force acts on the string 22 and suppresses a force that moves the absorbent body 21 and the first retaining table 120a to the front end side in the longitudinal direction. As a result, the second retaining table 120b tries to press the first retaining table 120a toward the front end side in the longitudinal direction, and the first retaining table 120a tries to return to the rear end side in the longitudinal direction due to the tensile force of the string 22. Accordingly, a compressive force acts on the load cell 127 between the first retaining table 120a and the second retaining table 120b.

On the other hand, in the case that the string 22 has not been properly attached to the absorbent body 21 (FIG. 10B), the force of the second retaining table 120b pressing the first retaining table 120a toward the front end side in the longitudinal direction cannot be suppressed by the tensile force of the string 22. As a result, the first retaining table 120a is pressed by the second retaining table 120b with no resistance, and is moved to the front end side in the longitudinal direction. Accordingly, a compressive force corresponding to the force of the piston rod 122b pressing the second retaining table 120b does not act on the load cell 127 between the first retaining table 120a and the second retaining table 120b.

Thus, it may be determined that the string 22 has been properly attached to the absorbent body 21 in the case that a predetermined compressive force acts on the load cell 127 as a result of increasing the distance between the tampon retaining sections 121a and 121b (the second retaining table 120b) and the string holding section 125, and it may be determined that the string 22 has not been properly attached to the absorbent body 21 in the case that the predetermined compressive force does not act on the load cell 127 as a result of increasing the distance.

Regarding a Tampon 10' without the Applicator 30

Figure 11A:
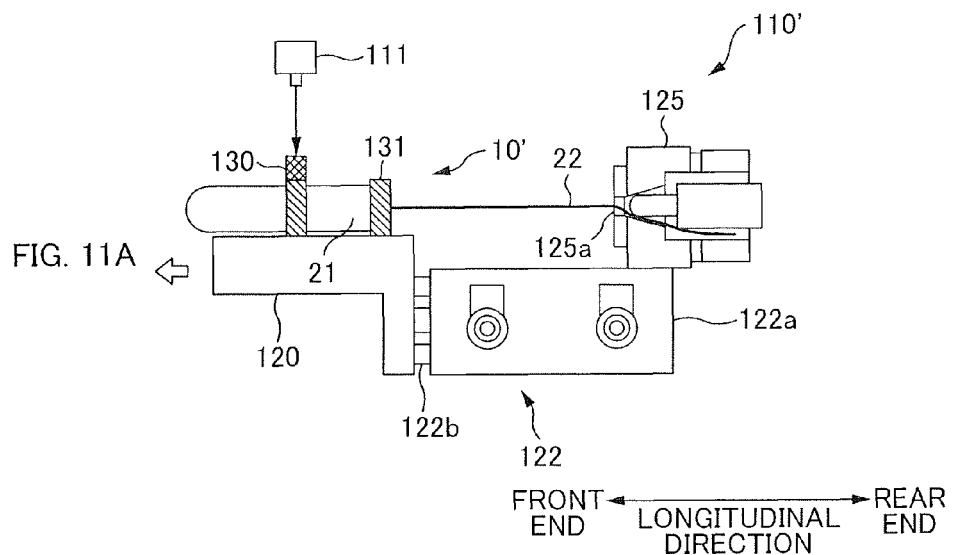
FIGS. 11A and 11B show views illustrating a string tensile test on a non-applicator tampon.
Figure 11B:
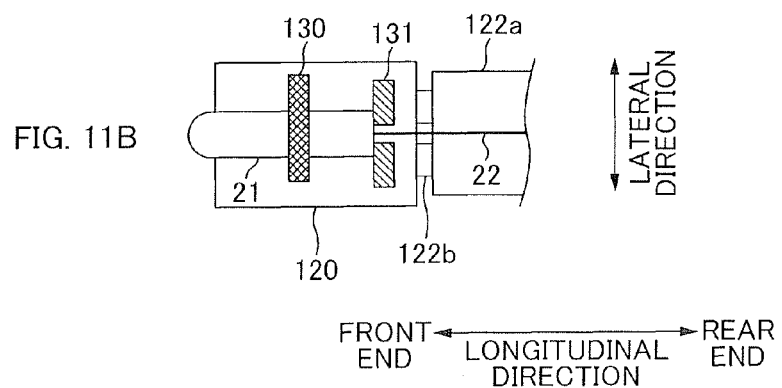

FIGS. 11A and 11B show views illustrating a string tensile test on a tampon 10' without the applicator 30. FIG. 11A is a view showing the configuration of a string pulling unit 110', and FIG. 11B is a view showing a state in which movement of the absorbent body 21 is regulated viewed from above. Although the description above concerns the string tensile test on the tampon 10 in which the tampon main body 20 (the absorbent body 20 and the string 22) is contained inside the applicator 30, in the following description, the tampon 10' having the absorbent body 21 and the string 22, that is, the tampon 10' without the applicator 30 will be described. A test device having the same configuration as that of the string pulling unit 110 in FIG. 5A used for the tampon 10 with the applicator 30 can be used to perform the string tensile test also on the tampon 10 without the applicator 30. Note that, as shown in FIG. 11, this device adopts a different method for regulating movement of the absorbent body 21.

In the string pulling unit 110' shown in FIG. 11, a front end-side tampon retaining section 130 (corresponding to a regulation section) that regulates movement of the absorbent body 21 and a rear end-side tampon retaining section 131 (corresponding to a regulation section) are provided on the retaining table 120. The front end-side tampon retaining section 130 is configured by a pair of protruding sections and a releasable clamp placed over the protruding sections. The absorbent body 21 is positioned between the protruding sections of the front end-side tampon retaining section 130. Meanwhile, the rear end-side tampon retaining section 131 is configured by a pair of protruding sections, and the string 22 is positioned between the protruding sections. The distance in the lateral direction between the protruding sections of the rear end-side tampon retaining section 131 is less than the outer diameter of the absorbent body 21, and, when a tensile force acts on the string 22, and a force that moves the absorbent body 21 to the rear end side in the longitudinal direction acts, the rear end section of the absorbent body 21 is brought into contact with the end face on the front end side of the rear end-side tampon retaining section 131. Thus, the rear end-side tampon retaining section 131 can regulate the movement of the absorbent body 21 to the rear end side in the longitudinal direction.

In the string pulling unit 110', first, the string 22 is held by the string holding section 125 while air is sucked by the suction section 126 from the rear end side of the absorbent body 21 (FIG. 5B). Subsequently, air is supplied to the movable air cylinder 122, and a force that causes movement to the front end side in the longitudinal direction acts on the retaining table 120 and the tampon 10' retained on the retaining table 120. In this manner, the distance in the longitudinal direction between the front end-side tampon retaining section 130 and the rear end-side tampon retaining section 131, and the string holding section 125 is increased, and, therefore, a tensile force is applied to the string 22. Then, it may be determined whether or not the string 22 has been properly attached based on the amount of change in the distance before and after increasing the distance in the longitudinal direction between the front end-side tampon retaining section 130 and the rear end-side tampon retaining section 131, and the string holding section 125. In the case that the amount of change in the distance is a threshold value or less, it can be determined that the string 22 has been properly attached, and, in the case that the amount of change in the distance is greater than the threshold value, it can be determined that the string 22 has not been properly attached. Furthermore, the sensor 111 may be positioned at a location where it can detect the front end-side tampon retaining section 130 as shown in FIG. 11A before the distance between the front end-side tampon retaining section 130 and the rear end-side tampon retaining section 131, and the string holding section 125 is increased, and it may be determined whether or not the string 22 has been properly attached based on whether or not the sensor 111 detects the front end-side tampon retaining section 130 after the distance is increased.

Note that, as shown in FIG. 1B, the absorbent body 21 is formed by covering the absorbent body material 211 with the cover member 212, attaching the string 22 thereto, and compressing the obtained material substantially into a cylinder. The tampon 10' without the applicator 30 may be individually wrapped in a state where the string 22 is rolled up at the rear end of the absorbent body 21. In the production of such a tampon 10', when compressing the absorbent body 21, press molding may be performed in a state where the string 22 is rolled up. Accordingly, in the case that the tensile test is performed on the string 22 after the absorbent body 21 is compressed as in FIG. 11, it is necessary to perform an operation that unrolls the rolled string 22 and performs the tensile test and then rolls up the string 22 after the test. Thus, the tensile test may be performed on the string 22 after the string 22 is attached to the absorbent body 21 and before the compression process is performed. Note that, in the case that the tensile test is performed on the string 22 after the absorbent body 21 is compressed as in FIG. 11, defects caused by the string 22 being damaged in the compression process can be detected. Furthermore, even in the case of the above-described tampon 10 with the applicator 30, the tensile test may be performed on the string 22 before the absorbent body 21 is contained inside the applicator 30 as in FIG. 11.

Other Embodiments

Although the tampon producing method and the tampon producing apparatus according to the invention were described based on the foregoing embodiment, this embodiment is merely for the purpose of elucidating the invention and is not to be interpreted as limiting the invention. The invention can of course be altered and improved without departing from the gist thereof and includes functional equivalents.

REFERENCE SIGNS LIST

10 Tampon, 20 Tampon main body, 21 Absorbent body, 211 Absorbent body material, 212 Cover member, 22 String, 30 Applicator, 40 Outer tube member (outer tube), 41 Large-diameter section, 42 Small-diameter section, 43 Front end opening, 44 Incision, 45 Stepped portion, 50 Movable member (inner tube), 51 Catch section, 52 Ring-like protrusion, 100 Tampon producing apparatus, 101 Compression molding drum, 102 Retaining mechanism, 103 Heat drum, 104 Retaining mechanism, 105 Assembly unit, 105a First conveyer, 105b Second conveyer, 106 Intermediate roller, 106a Rotational member, 106b First outer wall, 106c Second outer wall, 107 Front end molding unit, 107a Heating drum, 107b Cooling drum, 108 Rotating drum, 109 String test unit (test device), 110 String pulling unit, 111 Sensor, 112 Defective product discharge section, 113 Transport belt, 120 Retaining table, 121a Tampon retaining section (regulation section), 121b Tampon retaining section (regulation section), 122 Movable air cylinder, 122a Main body section, 122b Piston rod, 122c Piston unit, 123 String holding mechanism, 124 String holding air cylinder, 124a Rod section, 125 String holding section (holding section), 125a Hole, 125b Funnel section, 126 Suction section, 120a First retaining table, 120b Second retaining table, 127 Load cell, 130 Front end-side tampon retaining section (regulation section), 131 Rear end-side tampon retaining section (regulation section)

The invention claimed is:

1. A method for producing a tampon including
an absorbent body configured to absorb fluid, and
a string that is attached to the absorbent body,
the method comprising:
  attaching the string to the absorbent body;
  causing a regulation section to regulate movement of the absorbent body;
  causing a holding section to hold the string; and
  applying a tensile force to the string by increasing a distance in a longitudinal direction of the absorbent body between the regulation section and the holding section,
  wherein
  the tampon further has an applicator provided with
    an outer tube that contains the absorbent body, and
    an inner tube that is moveable inside the outer tube to push out the absorbent body from a front end of the outer tube,
  the string is exposed from a rear end of the inner tube, and
  the method further comprises causing the regulation section to
    regulate movement of the applicator, and
    regulate the movement of the absorbent body by causing an end face of the inner tube to contact the absorbent body.

2. A method for producing a tampon according to claim 1, wherein the string is held by the holding section while air is sucked by a suction section from a side of the absorbent body from which the string is extended.

3. A method for producing a tampon including
an absorbent body configured to absorb fluid, and
a string that is attached to the absorbent body,
the method comprising:
  attaching the string to the absorbent body;
  causing a regulation section to regulate movement of the absorbent body;
  causing a holding section to hold the string;
  applying a tensile force to the string by increasing a distance in a longitudinal direction of the absorbent body between the regulation section and the holding section; and
  detecting an attachment failure of the string with respect to the absorbent body based on an amount of change in the distance in the longitudinal direction between the regulation section and the holding section before and after increasing the distance.

4. A method for producing a tampon including
an absorbent body configured to absorb fluid, and
a string that is attached to the absorbent body,
the method comprising:
  attaching the string to the absorbent body;
  causing a regulation section to regulate movement of the absorbent body;
  causing a holding section to hold the string; and
  applying a tensile force to the string by increasing a distance in a longitudinal direction of the absorbent body between the regulation section and the holding section,
  wherein a defective product discharge section is provided to discharge, out of a production process, a tampon in which there is an attachment failure of the string with respect to the absorbent body, as a result of increasing the distance, and
  the method further comprises:
    calculating a point in time when a given tampon reaches the defective product discharge section; and
    causing the defective product discharge section to discharge, out of the production process, the given tampon at the calculated point in time, in a case where there is an attachment failure of the string with respect to the absorbent body of the given tampon.

5. A method for producing a tampon including
an absorbent body configured to absorb fluid, and
a string that is attached to the absorbent body,
the method comprising:
  attaching the string to the absorbent body;
  causing a regulation section to regulate movement of the absorbent body;
  causing a holding section to hold the string; and
  applying a tensile force to the string by increasing a distance in a longitudinal direction of the absorbent body between the regulation section and the holding section,
  wherein
  one of the regulation section and the holding section is a fixed section whose position is fixed,
  another one of the regulation section and the holding section is a movable section configured to move in the longitudinal direction,
  a sensor is positioned at a location that is off the fixed section toward the movable section by a predetermined distance, and
  the method further comprises detecting an attachment failure of the string with respect to the absorbent body based on a detection result of the sensor after the distance is increased.

6. A method for producing a tampon according to claim 5, wherein
  the movable section is positioned at a location where the sensor detects the movable section before the distance is increased, and
  the movable section is positioned at a location where the sensor does not detect the movable section after the distance is increased, in a case where there is an attachment failure of the string.

7. A method for producing a tampon according to claim 5, wherein
  the movable section is positioned at a location where the sensor detects the movable section before the distance is increased, and
  the movable section is positioned at a location where the sensor detects the movable section after the distance is increased, in a case where the string has been properly attached and is held with slack by the holding section.

8. An apparatus for producing a tampon including
  an absorbent body configured to absorb fluid, and
  a string that is attached to the absorbent body,
the apparatus comprising:
  an attachment device configured to attach the string to the absorbent body;
  a regulation section configured to regulate movement of the absorbent body;
  a holding section configured to hold the string; and
  a test device configured to apply a tensile force to the string by increasing a distance in a longitudinal direction of the absorbent body between the regulation section and the holding section,
wherein
the tampon further has an applicator provided with
  an outer tube that contains the absorbent body, and
  an inner tube that is moveable inside the outer tube to push out the absorbent body from a front end of the outer tube,
the string is exposed from a rear end of the inner tube, and
the regulation section is configured to
  regulate movement of the applicator, and
  regulate the movement of the absorbent body by causing an end face of the inner tube to contact the absorbent body.

\* \* \* \* \*